United States Patent [19]

Hedner

[11] Patent Number: 5,180,583

[45] Date of Patent: Jan. 19, 1993

[54] METHOD FOR THE TREATMENT OF BLEEDING DISORDERS

[76] Inventor: Ulla K. E. Hedner, Bagangsvagen 29, SE-21620 Malmo, Sweden

[21] Appl. No.: 666,423

[22] Filed: Mar. 8, 1991

Related U.S. Application Data

[63] Continuation of Ser. No. 368,967, Jun. 19, 1989, abandoned, which is a continuation of Ser. No. 933,408, Nov. 20, 1986, abandoned.

[30] Foreign Application Priority Data

Nov. 26, 1985 [DK] Denmark .............................. 5446/85
Sep. 26, 1986 [DK] Denmark .............................. 4592/85

[51] Int. Cl.⁵ .................. A61K 37/547; A61K 35/16; C07K 15/06
[52] U.S. Cl. ............................. 424/94.64; 514/802; 514/2; 514/21; 530/381; 530/384
[58] Field of Search ............... 424/94.64; 530/381, 530/384; 514/802, 2, 21

[56] References Cited

U.S. PATENT DOCUMENTS

| | | | |
|---|---|---|---|
| 4,287,180 | 9/1981 | Thomas | 424/101 |
| 4,298,598 | 11/1981 | Schwarz et al. | 424/101 |
| 4,363,319 | 12/1982 | Altshuler | 435/214 |
| 4,382,083 | 5/1983 | Thomas | 424/101 |
| 4,391,746 | 7/1983 | Mita et al. | 424/101 |
| 4,456,591 | 6/1984 | Thomas | 424/101 |
| 4,470,968 | 9/1984 | Mitra et al. | 424/101 |
| 4,470,969 | 9/1984 | Pancham et al. | 424/101 |
| 4,473,553 | 9/1984 | Zuffi et al. | 424/101 |
| 4,479,938 | 10/1984 | Thomas | 424/101 |
| 4,663,164 | 5/1987 | Thomas | 424/101 |

OTHER PUBLICATIONS

Basic and Clinical Immunology, 5th Ed. Stites et al, eds., pp. 482–484, 1984.

Primary Examiner—Jacqueline Stone
Attorney, Agent, or Firm—Steve T. Zelson; Elias J. Lambiris

[57] ABSTRACT

A method for treating patients suffering from bleeding disorders not caused by clotting factor defects or clotting factor inhibitors, as well as a novel composition for use in treating bleeding disorders as disclosed. The method includes administering to a patient a composition comprising an effective haemostatic amount of factor VIIa, and is particularly effective in treating patients suffering from thrombocytopenia and von Willebrand's disease, as well as other platelet disorders. A composition suitable for use in treating such bleeding disorders comprises purified factor VIIa in a concentration of at least 25 μg/ml.

9 Claims, No Drawings

METHOD FOR THE TREATMENT OF BLEEDING DISORDERS

This application is a continuation of co-pending U.S. application Ser. No. 07/368,967 filed Jun. 19, 1989 now abandoned which is a continuation of U.S. application Ser. No. 06/933,408 filed Nov. 20, 1986, now abandoned.

1. Technical Field

The present invention is generally directed toward the use of factor VIIa for the treatment of patients suffering from bleeding disorders, such as platelet disorders, including thrombocytopenia, von Willebrand's disease, and others typically present in association with severe tissue damage. In accordance with the present invention, factor VIIa may also be used for the treatment of gastrointestinal bleedings and nasal-oral bleedings, even in cases where no specific basic haemostatic disorders have been diagnosed.

2. Background Art

Uncontrolled and excessive bleeding is a major problem both in connection with surgery and also various forms of tissue damage. Bleeding disorders may be caused by clotting factor deficiencies or clotting factor inhibitors (haemophilia A and B). Bleeding disorders are, however, also seen in patients not suffering from haemophilia A or B, for example, in patients suffering from von Willebrand's disease. Patients with von Willebrand's disease have a defective primary haemostasis because they lack or have an abnormal von Willebrand factor protein. Bleeding disorders are also seen in patients with a normally functioning blood clotting cascade and may be caused by a defective platelet function, thrombocytopenia, or even by unknown reasons.

Clot formation is basically induced by the conversion of the soluble plasma protein fibrinogen into insoluble fibrin, catalyzed by the enzyme thrombin. The blood components which participate in the coagulation cascade are proenzymes or zymogens, enzymatically inactive proteins which are converted to proteolytic enzymes by the action of an activator, itself an activated clotting factor. Coagulation factors which have undergone such a conversion are generally referred to as "activated factors," and are designated by the addition of a lower case postscript "a"(e.g., VIIa).

There are two separate systems which can promote blood clotting. These systems are referred to as the intrinsic and the extrinsic coagulation pathways. In the intrinsic pathway, only factors present in plasma are utilized. An intermediate event in the intrinsic pathway is the activation of factor IX to factor IXa, a reaction catalyzed by factor XIa and calcium ions. Factor IXa then participates in the activation of factor X to factor Xa in the presence of factor VIIIa, phospholipid and calcium ions. The extrinsic pathway involves plasma factors as well as components present in tissue extracts. Factor VII, one of the proenzymes referred to above, participates in the extrinsic pathway of blood coagulation by converting (upon its activation to VIIa) factor X to Xa in the presence of tissue factor and calcium ions. Factor Xa in turn then converts prothrombin to thrombin in the presence of factor Va, calcium ions and phospholipid. Because the activation of factor X to factor Xa is an event shared by both the intrinsic and extrinsic pathways, factor VIIa may be used for the treatment of patients with deficiencies or inhibitors of factor VIII (U.S. Pat. No. 4,382,083) and factor VIIa has been shown to be capable of by-passing the initial phase of the coagulation cascade in haemophilia A patients with antibodies against VIII:C, Hedner and Kisiel, *J. Clin. Invest.* 71: 1836–1841, 1983.

Thrombocytopenia, defined as "a decreased number of circulating platelets," is a common clinical problem associated with a diverse group of diseases and complex situations in which multiple factors contribute to the low platelet count. Lowered platelet counts result in an increased bleeding tendency manifesting itself in mucosal bleedings from, for example, the nasal-oral area or the gastrointestinal tract, as well as in oozing from wounds, ulcers and injection sites. Thrombocytopenic bleeding can be extensive and create serious problems both during surgery and also postoperatively. Even minor surgery such as tooth extractions may cause severe bleeding. Furthermore, spontaneous intracranial bleeding may occur at extremely low platelet counts ($<10\times10^9/1$).

A decreased number of circulating platelets may be the result of: (1) a production defect, (2) an abnormal distribution, (3) a dilutional loss (massive blood transfusion), or (4) an abnormal destruction.

A defective production of platelets in the bone marrow may be the result of a variety of conditions, including the influence of toxic agents, such as irradiation, cytostatics, certain drugs, etc., tumor infiltrations (metastatic cancer and leukaemia), or degenerative processes of unknown origin (often associated with anaemia or other blood disorders). An abnormal distribution of platelets is seen in association with haemotologic disorders (leukaemia, myeloma, lymphoma), liver diseases, tumors, etc. In these situations, the platelets may be trapped in an enlarged spleen or liver and thus escape from the circulating blood. Massive blood transfusion without special addition of fresh platelets will result in a lowered concentration of platelets in the circulating blood and is thought to be the cause of thrombocytopenic bleedings that may occur in such situations. An abnormal destruction of platelets may be the result of: (1) an increased consumption in vessel grafts or in traumatized tissue or (2) an immune mechanism as may be seen in drug-induced thrombocytopenia, idiopathic thrombocytopenic purpura (ITP), autoimmune disease, haematologic disorders (leukaemia, lymphoma), etc.

Platelets are of importance for the primary haemostasis by inducing the formation of a primary haemostatic plug that subsequently is solidified through the activation of the coagulation cascade and the formation of fibrin. The platelets normally provide coagulation factors, including factor V, factor VII, and fibrinogen, as well as phospholipids that are necessary for the initiation of local haemostasis.

In patients suffering from thrombocytopenia, the normal coagulation cascade is put out of function due to the lack of initiation of the primary steps of the coagulation cascade. The treatment of such patients often meets with substantial difficulties. Patients with thrombocytopenia are at present most commonly treated by the administration of platelet concentrates prepared from donor blood. Such concentrations consist of pooled platelets from 5–6 donors. Most repeated recipients of platelet transfusions develop antibodies against platelet antigens, resulting in a poor or totally absent effect of further platelet transfusions. There is presently no suitable treatment to be offered to such patients.

A defective platelet function is rather common both as a congenital disorder (Glanzmann's thrombastenia, other congenital forms of thrombastenia, platelet aggregation defects) and as a complication to a number of diseases such as leukaemia, dysproteinaemia (e.g., myeloma), autoimmune diseases (rheumatoid arthritis, systemic lupus erythematosus, etc.) and uraemia. Patients with a defective platelet function may develop bleedings mostly of a mucosal type, as described above for those with thrombocytopenia. In association with surgery, these patients also need treatment to avoid excessive bleeding. Currently, antifibrinolytic treatment (tranexamic acid, ε-aminocaproic acid) is used alone or together with the administration of desmopressin (DDVAP), a vasopressin analogue. However, desmopressin also has cardiovascular effects resulting in vasoconstriction. This makes the drug unsuitable for use in patients suspected to have some sort of cardiovascular problem.

Patients with von Willebrand's disease have a defective primary haemostasis because they lack or have an abnormal von Willebrand factor protein. Patients with von Willebrand's disease consequently have mucosal bleedings both from the nasal-oral area and the gastrointestinal tract. Those having the most severe forms of von Willebrand's disease also suffer from joint bleedings. In patients with von Willebrand's disease, a factor capable of inducing haemostasis through by-passing the initial haemostatic steps may be beneficial.

Consequently, there is a need in the art for an improved method of treating patients with a defective platelet function, as well as those patients suffering from thrombocytopenia and von Willebrand's disease, that does not suffer from the unwanted side effects and inconveniences characteristic of prior treatments. The present invention fulfills this need and further provides other related advantages, including a method for treating gastrointestinal and nasal-oral bleedings, even in situations where no specific haemostatic disorders have been diagnosed.

DISCLOSURE OF THE INVENTION

Briefly stated, the present invention discloses a method for treating patients suffering from bleeding disorders not caused by clotting factor defects or clotting factor inhibitors as well as a novel composition for use therein. The method generally comprises administering to the patient a composition comprising an effective haemostatic amount of factor VIIa. The composition may also include a physiologically acceptable carrier or diluent, or an adjuvant. Suitable adjuvants include albumin, non-reducing sugars, polyalcohols, polysaccharides and antioxidants.

The method set forth herein is particularly effective in treating patients suffering from thrombocytopenia, von Willebrand's disease, as well as other platelet disorders. In addition, the method may be used to treat patients suffering from gastrointestinal bleedings or nasal-oral bleedings.

In a preferred embodiment of the method of the present invention, the composition is administered intravenously, and in an amount from about 100 units to 1,000 units of factor VIIa per kilogram of body weight, and more preferably, 100 units to 500 units. The composition is preferably administered during a time period of approximately 24 hours.

A related aspect of the present invention discloses a novel composition suitable for use in treating bleeding disorders as well as the methods described herein comprising purified factor VIIa in a concentration of at least 25 ug/ml.

It will be appreciated by those skilled in the art that, for ease of administration, it is preferable to utilize a concentration of factor VIIa of approximately 25 ug/ml–500 ug/ml, and more preferably, a concentration of 25 ug/ml–200 ug/ml, although significantly higher concentrations could be used within the present invention. The use of concentrations as described above allows convenient infusions of from 1–5 ml per dose.

Other aspects of the present invention will become evident upon reference to the following detailed description.

BEST MODE FOR CARRYING OUT THE INVENTION

In its broadest aspect, the present invention provides a method for treating patients suffering from bleeding disorders not caused by clotting factor deficiencies or clotting factor inhibitors. Within this method, a composition which includes an activated haemostatic agent containing an effective amount of factor VIIa is administered to the patient.

The composition may contain unactivated factor VII and other unactivated blood coagulation factors, such as factor IX, which may enhance the activity of factor VIIa. The factor IX concentration should preferably be in a range that corresponds to a given dose of about 10 units per kilogram body weight. It s preferred that factor VIIa be unaccompanied by blood coagulation factors other than factor IX.

Human purified factor VIIa is preferably made by the methods described by Broze and Majerus, *J. Bio. Chem.* 255, 4: 1242–1247, 1980, and Hedner and Kisiel, *J. Clin. Invest.* 71: 1836–1841, 1983. These methods yield factor VII without detectable amounts of other blood coagulation factors. An even further purified factor VII preparation may be obtained by including an additional gel filtration as the final purification step. Factor VII is then converted into activated factor VIIa by known means, e.g. by several different plasma proteins, such as factor XIIa, IXa or Xa. Alternatively, as described by Bjoern et al., ("Activation of Coagulation Factor VII to VIIa,"*Research Disclosure* 269:564–565, 1986), factor VII may be activated by passing it through an ion-exchange chromatography column, such as MonoQ (Pharmacia Fine Chemicals, Uppsala, Sweden) or the like. It will be appreciated by those skilled in the art that a suitable factor VIIa for use in the present invention may also be produced by recombinant DNA technology, e.g., by insertion of the cDNA or gene encoding factor VII (Hagen et al., *Proc. Natl. Acad. Sci. USA* 83: 2412–2416, 1986) in a suitable vector, transforming of suitable cell lines with the vector and growing the transformed cells in an appropriate medium whereupon the expressed product is isolated and activated into factor VIIa. Factor VIIa produced by recombinant DNA technology may be authentic factor VIIa or a more or less modified factor VIIa, provided that such modified factor VIIa has substantially the same biological activity for blood coagulation as authentic factor VIIa. Such modified factor VIIa may be prepared by modifying the DNA sequence encoding factor VII either by altering the amino acid codons or by removal of some of the amino acid codons in the natural gene by known means, e.g., by site-specific mutagenesis.

It is evident that the practice of the methods described herein is independent of how the factor VIIa is derived and, therefore, the present invention is contemplated to cover the use of any factor VIIa preparation suitable for use herein.

According to the present invention, factor VIIa is shown to be capable of arresting bleeding, even in patients that have virtually no circulating platelets. Briefly, purified factor VIIa was injected into rabbits made thrombocytopenic by anti-platelet serum, and the experiments demonstrated that trace amounts of purified human factor VIIa effectively arrested bleeding in the thrombocytopenic animals. Factor VIIa is thus capable of by-passing the primary haemostasis and may cause local haemostasis without the participation of platelets and the initial coagulation phase. Factor VIIa is also shown to be able to induce local haemostasis in human patients suffering from thrombocytopenia.

Patients suffering waste tissue damage with a massive cell destruction may develop complex haemostatic disorders as a result of the release of a variety of enzymes from the disrupted cells. Such enzymes may influence both the coagulation and fibrinolytic systems, leading to a degradation of several factors involved with one system or the other. It may also be beneficial to use factor VIIa in these patients due to the capability of VIIa to produce a haemostatic plug through activation of the latter phases of the coagulation system. Treatment using factor VIIa in this regard may be through intravenous injection or application locally, and may be combined with anti-fibrinolytic therapy. Further, in any bleeding situation, e.g., gastrointestinal or nasal-oral bleedings or in surgery, it may be beneficial to use factor VIIa in substantially the same concentrations as described herein, thus inducing local haemostasis. Factor VIIa may be applied locally or intravenously in these situations.

Factor VIIa is generally administered by intravenous injections and in an amount approximately 100–1000 units per kilogram body weight, and preferably, in an amount of about 100–500 units per kg body weight corresponding to about 2–5 ug/kg. A dose of 2–5 ug/kg may have to be repeated 2–4 times/24 hours.

"One unit," as used herein, is defined as the amount of factor VII present in 1 ml of normal plasma, corresponding to about 0.5 ug protein. After activation, 50 units corresponds to about 1 ug protein.

A "haemostatic effect" or "amount," as used herein, is defined as the substantial cessation of bleeding within 15 minutes after administration of about 100–1000 u/kg body weight of pure factor VIIa.

Another aspect of the present invention provides a method for preparing a pharmaceutical composition for the treatment of bleeding disorders in which factor VIIa, preferably in a purified form, is mixed with suitable adjuvants or a suitable carrier or diluent. Suitable physiologically acceptable carriers or diluents include sterile water and saline. Suitable adjuvants, in this regard, include calcium, albumins, or other inert proteins to stabilize the factor VIIa. Other physiologically acceptable adjuvants are non-reducing sugars, polyalcohols (such as sorbitol or glycerol), polysaccharides (such as low molecular weight dextrins), amino acids, and antioxidants (such as bisulfite and ascorbate). The adjuvants are generally present in a concentration of from 0.1%–3% w/v. The pharmaceutical composition may also contain protease inhibitors, e.g., aprotinin. In a particularly preferred embodiment, calcium is used in combination with another selected adjuvant within the pharmaceutical composition. The amount of calcium is preferably 5–50 mM, more preferably 10–20 mM.

The following examples are offered by way of illustration, and not by way of limitation.

EXAMPLE 1

Rabbits were made thrombocytopenic by the administration of sheep antibodies against rabbit platelets prepared by the methods of Busch et al., *Acta Chir. Scand.* 140: 255, 1974. Haemostatic plug formation in the rabbit meseteric microvessels was studied by the method of Bergqvist and Arfors, *Thromb. Diathes. Haemorrh.* 30: 586, 1973. For each observation time, three arterioles and three venules (diameter 20–40 um) were transected and the time for haemostatic plug formation was measured and the frequency of rebleeding recorded. The time required for primary haemostatic plug formation was defined as "the interval between transection and the first arrest of bleeding." The sum of this and all the rebleeding times was called the "total haemostatic plug formation time" (THT). The platelet counts in the rabbits decreased to a minimum 15–60 minutes after the antiplatelet serum was administered and remained low throughout the observation period. In the control animals, a decrease from $263 \times 10^9/l$ (mean value) to $10 \times 10^9/1$ (mean value) occurred. Before the platelet antibodies were administered, the THT in the arterioles (THT-A) showed a mean of 54 s. A greater than threefold prolongation of THT-A to 179 seconds was observed 15 minutes as well as 60 minutes after the antibody administration. The THT in the venules (THT-V) varied between 202 and 394 s (mean 274 s) prior to antibody administration. In parallel with the prolongation of THT-A, a prolongation of the THT-V (mean 768 s) 15 minutes after the antibody administration was observed and stayed relatively constant throughout the observation time.

Three rabbits were made thrombocytopenic in the same way as the control animals, and human factor VIIa (50 u/kg b.w.) was then administered (30 minutes after the antibody) Ten minutes after the factor VIIa was injected, the THT-A values showed a substantial shortening in each rabbit (mean 114 s; mean after the antibody administration 260 s prior to factor VIIa). The shortening was, however, transient (mean 30 minutes after the factor VIIa was 219 s). The THT-V showed a similar pattern with a shortening 10 minutes after the factor VIIa (mean after the antibody administration 698 s and 10 minutes after the factor VIIa 499 s). The slight shortening was transient; and 30 minutes after the factor VIIa injection, the THT-V showed a mean of 672 s.

Another 5 thrombocytopenic rabbits were then given twice as much factor VIIa (100 u/kg b.w.); and ten minutes after the factor VIIa was given, the THT-A showed a marked shortening from a mean of 256 s after the antibody administration to a mean of 89 s ten minutes after the factor VIIa. This shortening persisted throughout the observation time. The THT-V was markedly shortened following the injection of factor VIIa (from a mean of 591 s after the antibody administration to a mean of 390 s). After 30 minutes, a normalization of the THT-V had occurred (mean 255 s) and the same was observed after 60 minutes (mean 299 s).

No effect on the THTs was noted in 5 non-thrombocytopenic rabbits. When factor VII was given rather than factor VIIa, no effect on the THT was seen.

The results are summarized in the following table:

TABLE

The THT-A and THT-V in 5 rabbits before and after APS followed by administration of factor VIIa (100 u/kg b.w.). The means of 3 transsections at each checkpoint are given. The numbers within parentheses are the values obtained in 3 thrombocytopenic rabbits given factor VII in a dose of 60 u/kg b.w.

| Rabbit No. | | Before | 15 minutes after APS | 30 minutes after APS 10 minutes after Factor VIIa (VII) (100 u/kg b.w.) | 60 minutes after APS 30 minutes after Factor VIIa (VII) (100 u/kg b.w.) | 90 minutes after APS 60 minutes after Factor VIIa (VII) (100 u/kg b.w.) |
|---|---|---|---|---|---|---|
| THT-A | 1 | 42 (77) | 131 (225) | 89 (288) | 111 (144) | — |
|  | 2 | 63 (57) | 483 (222) | 104 (256) | 153 (87) | 86 |
| (sec) | 3 | 90 (75) | 206 (763) | 81 (717) | 119 (631) | 210 |
|  | 4 | 61 | 179 | 77 | 50 | 72 |
|  | 5 | 53 | 279 | 95 | 95 | 110 |
| mean |  | 65 (70) | 256 (403) | 89 (420) | 106 (364) | 102 |
| THT-V | 1 | 277 (176) | 719 (580) | 485 (900) | 253 (411) | — |
|  | 2 | 164 (321) | 463 (768) | 357 (812) | 187 (657) | 236 |
|  | 3 | 254 (230) | 585 (899) | 274 (900) | 288 (839) | 243 |
|  | 4 | 213 | 599 | 551 | 155 | 229 |
|  | 5 | 376 | 590 | 285 | 391 | 487 |
| mean |  | 257 (242) | 591 (749) | 390 (871) | 255 (636) | 299 |
| Platelet count × $10^9$/l |  |  |  |  |  |  |
| mean |  | 222 (193) | 2 (6) | 2 (8) | 6 (25) | 10 |
| range |  | 243–214 (93–283) | 0–8 (2–9) | 1–2 (2–12) | 5–10 (18–23) | 7–12 |

The present experiments demonstrate the important role of factor VIIa in the initiation of the coagulation process in vivo. In contrast, factor VII had little if any effect in this process. Furthermore, factor VIIa was capable of initiating the coagulation process in the absence of platelets. Accordingly, the phospholipid normally provided at the site of injury by the platelets is made available from damaged endothelial cells that also provide the tissue factor.

EXAMPLE 2

Two human patients having haematological disorders (macroglobulinaemia Waldenstrom and chronic lymphatic leukaemia, respectively) complicated with severe thrombocytopenia (platelet count $<10 \times 10^9$/l) were given factor VIIa purified from human plasma principally according to the method described by Hedner and Kisiel (supra).

The first patient was treated in association with a profuse nose bleeding. The bleeding time (BT) according to Duke was >15 minutes before the injection of the factor VIIa as a result of the severe thrombocytopenia. A dose of 100 u/kg b.w. (2 ug/kg b.w.) was given intravenously, and 15 minutes after the completion of the injection, the Duke BT was normalized (4 minutes; normal range: <5 minutes).

The platelet count stayed the same ($10 \times 10^9$/l) throughout the observation time. The nose bleeding stopped promptly, and the clots formed could be removed without any bleeding. A small rebleeding started later but stopped spontaneously. No influence on the pulse, temperature, or blood pressure was observed. The factor VII level in plasma rose from 0.66 u/ml to 2.07 u/ml and was again 0.60 at 8 hours after the injection. No influence on the plasma level of factor X (1.12 u/ml before and 1.12 u/ml after the injection) was seen remaining at the same level for the 8 hour observation time. No fibrin/fibrinogen degradation products appeared in the circulation and the ethanol gelation test stayed negative throughout. Furthermore, no changes in ATIII or $\alpha_2$AP were observed.

Patient no. 2 also had a platelet count of $<10 \times 10^9$/l and a Duke BT of >15 minutes before the injection of Factor VIIa. The patient bled profusely from the Duke incision in the ear, a bleeding that had to be stopped by manual compression and the local application of thrombin. Factor VIIa in a pure form was given intravenously in a dose of about 100 u/kg b.w. (2 ug/kg b.w.), and the Duke BT was repeated 15 minutes after the completion of the injection. The Duke BT was then 10 minutes, and the formation of a visible clot was observed on the site of the incision. No change of the platelet count was recorded; and no influence on the pulse, blood pressure, or body temperature occurred. The plasma level of factor VII rose from 0.57 u/ml to 2.17 u/ml. No change in the factor X level (0.73 u/ml before and 0.81 u/ml after the injection) and no change in ATIII or $\alpha_2$AP were seen.

In summary, purified factor VIIa injected intravenously shortened the prolonged BT in patients with severe thrombocytopenia. In parallel, an increase of the plasma level of factor VII was observed. No signs of a general effect on the coagulation mechanism were observed.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for treating patients suffering from a platelet disorder caused by impaired platelet function or a low number of circulating platelets but not caused by a blood clotting factor disorder, factor VIII:c deficiency or von Willebrand factor deficiency comprising administering to a patient suffering from said platelet disorder a composition comprising more than 125 units to about 1000 units of factor VIIa/kg of body weight together with a physiologically acceptable carrier or diluent.

2. The method of claim 1 wherein said patient suffers from bleeding in association with tissue damage.

3. The method of claim 1 wherein factor VIIa is administered by intravenous injection.

4. The method of claim 1 wherein said patient is administered from more than 125 units to about 500 units of factor VIIa/kg of body weight.

5. The method of claim 1 wherein said composition further includes factor IX.

6. The method of claim 1 wherein said composition includes an adjuvant.

7. The method of claim 6 wherein said adjuvant is calcium.

8. The method of claim 6 wherein said adjuvant is selected from the group consisting of albumin, non-reducing sugars, polyalcohols, amino acids, polysaccharides, and antioxidants.

9. The method of claim 1 wherein the platelet disorder is thrombocytopenia.

* * * * *